United States Patent [19]

Klein et al.

[11] Patent Number: 4,994,096
[45] Date of Patent: Feb. 19, 1991

[54] GAS CHROMATOGRAPH HAVING INTEGRATED PRESSURE PROGRAMMER

[75] Inventors: Kenneth J. Klein, Wilmington, Del.; R. John Phillips, Swarthmore, Pa.; Lesley M. Freed, Wilmington, Del.; Michael Thompson, Coatesville, Pa.

[73] Assignee: Hewlett-Packard Co., Palo Alto, Calif.

[21] Appl. No.: 349,740

[22] Filed: May 9, 1989

[51] Int. Cl.$^5$ .............................................. B01D 15/08
[52] U.S. Cl. .......................................... 55/20; 55/21; 55/67; 55/197; 55/270; 55/386
[58] Field of Search ................. 55/18, 20, 21, 67, 197, 55/208, 267–270, 386

[56]  References Cited

U.S. PATENT DOCUMENTS

| | | | |
|---|---|---|---|
| 3,174,326 | 3/1965 | Carle et al. | 55/67 X |
| 3,225,521 | 12/1965 | Burow | 55/67 |
| 3,305,000 | 2/1967 | Bullen et al. | 55/386 X |
| 3,496,702 | 2/1970 | Carel et al. | 55/67 |
| 3,527,567 | 9/1970 | Philyaw et al. | 55/67 X |
| 3,822,203 | 7/1974 | Annino et al. | 55/67 X |
| 4,035,168 | 7/1977 | Jennings | 55/197 X |
| 4,521,225 | 6/1985 | Jenkins et al. | 55/18 |
| 4,681,678 | 7/1987 | Leaseburge et al. | 55/386 X |
| 4,684,465 | 8/1987 | Leaseburge et al. | 55/386 X |
| 4,732,581 | 3/1988 | Cheh et al. | 55/67 |
| 4,774,190 | 9/1988 | Weiss | 55/67 X |
| 4,780,116 | 10/1988 | Cheh et al. | 55/197 X |
| 4,802,981 | 2/1989 | Kenney et al. | 55/386 X |
| 4,814,089 | 3/1989 | Kumar | 55/67 X |

OTHER PUBLICATIONS

Scott, R. P. W., "New Horizons In Column Performance", 5th International Symposium on Gas Chromatography as reported in Gas Chromatography 1964 by Goldup, pp. 32–37.
Costa Neto, C., et al., "Programmed Flow Gas Chromatography", Journal of Chromatography, vol. 15 (1986), pp. 301–313.
Zlatkis, A., "Flow Programming-A New Technique in Gas Chromatography", Journal of Chromatography (Mar. 1965), pp. 75–87.
Nygren, S. et al., "Flow Programming in Glass Capillary Column-Electron Capture Gas Valve in the Splitter Line," Journal of Chromatography, vol. 123 (1976), pp. 101–108.
Larson, J. R., et al., "Flow Programming System for Process Capillary Gas Chromatography", Journal of Chromatography, vol. 405 (1987), pp. 163–168.

Primary Examiner—Robert Spitzer
Attorney, Agent, or Firm—Richard F. Schuette

[57] ABSTRACT

Apparatus and methods are disclosed for performing a chromatographic separation of a given compound utilizing programmed temperature and mass flow wherein the compound is injected into a pressurized carrier gas and passed through a column and wherein a portion of the column is subjected to a temperature profile, by determining the pressure of the carrier gas and generating a pressure information signal representative of such pressure, storing desired carrier gas mass flow information and temperature profile information, and controlling the pressure of the carrier gas in response to the mass flow information, the temperature profile information and the pressure information signal, so that as the temperature profile information changes with time, the desired mass flow of carrier gas at a corresponding time is maintained by controlling the pressure of the carrier gas.

25 Claims, 4 Drawing Sheets

GAS CHROMATOGRAPH HAVING INTEGRATED PRESSURE PROGRAMMER

FIELD OF THE INVENTION

The present invention relates to an advancement in the art of Gas Chromatography (GC) and, more particularly, to a GC system having flow and temperature regulation capabilities.

BACKGROUND OF THE INVENTION

In analytical chemistry, liquid and gas chromatography techniques have become important tools in the identification of chemical sample components. The basic principle underlying all chromatographic techniques is the separation of a sample chemical mixture into individual components by transporting the mixture in a moving fluid through a porous retentive media. The moving fluid is referred to as the mobile phase and the retentive media has been referred to as the stationary phase. One of the differences between liquid and gas chromatography is that the mobile phase is either a liquid or a gas, respectively.

In a gas chromatograph, typically, a supply of inert carrier gas (mobile phase) is continually passed as a stream through a heated column containing porous sorptive media (stationary phase). GC columns have also been known to comprise a hollow capillary tube having an inner diameter in the range of few hundred microns. A sample of the subject mixture is injected into the mobile phase stream and passed through the column. As the subject mixture passes through the column, it separates into its various components. Separation is due primarily to differences in the volatility characteristics of each sample component with respect to the temperature in the column. A detector, positioned at the outlet end of the column, detects each of the separated components as they exit the column.

The analytical choice between liquid and gas chromatography techniques is largely dependent on the molecular weight of the compound being analyzed. Liquid chromatographs are capable of analyzing much heavier compounds than gas chromatographs. However, since gas chromatography detection techniques are more sensitive, they are preferred. Consequently, a need exists for a chromatographic device which is as sensitive as a GC device and is capable of analyzing compounds having heavier molecular weights than those now subject to GC analysis.

The advent of Supercritical Fluid Chromatography (SFC) provided a potential bridge between gas and liquid chromatography advantages, i.e., high sensitivity and heavier molecular weight samples. In SFC, a fluid heated above the critical point, is used as the mobile phase. Such fluid is passed under pressure through a media which differentially retains sample components. As the pressure of the mobile phase is increased, for example, from about 40 ATM to approximately 400 ATM, the sample being analyzed separates into its various components dependent upon the relative differential solubility of each component with the mobile phase. Since the mobile phase is a gas, detectors used in GC can be utilized, significantly enhancing detection sensitivity and selectivity.

SFC has been found to be primarily useful in the analysis of moderate molecular weight homologous series (M.W. 100 to 10,000) and some thermally labile molecules such as pesticides and pharmaceuticals. The problem with SFC, however, is the long period of time involved in conducting a sample analysis. Consequently, it is still desireable to provide a chromatographic device having the speed of GC techniques and which are capable of analyzing higher molecular weight compounds.

The present invention satisfies the above described need of increasing the speed and extending the molecular weight range of compounds capable of GC analysis by providing apparatus and methods which control the carrier gas (mobile phase) pressure in relation to programmed flow and temperature parameters in an open loop arrangement.

It has been known in the past to program temperature in gas chromatographic analyzation since separation of the sample components is due primarily to differences in the volatility characteristics of each component with respect to the temperature in the column. By raising the column temperature either in a constant linear fashion or in a variable non-linear fashion over a sufficient range of temperature one can assure high resolution detection of all sample components in a minimized time period. High resolution is assured because each component is emerging from the column at its optimum temperature.

As used herein the term resolution refers to the distinctness of graphed peaks generated by known detection apparatus, wherein each peak is representative of the detection of a sample component.

It has also been known in the past that the time required for a temperature programmed GC analysis can be reduced even further if carrier gas flow is programmed. Scott, R. P. W., New Horizons in Column Performance, 5th International Symposium on Gas Chromatography as reported in Gas Chromatography 1964 by Goldup, pp. 32-37 indicates that analysis time can be reduced by increasing the flow rate. However, while increasing the flow rate may reduce analysis time, efficiency is also reduced due to so-called overloaded components which results in poor resolution at detection. By customizing the temperature and flow programs for particular mixtures so that flow is increasing during the detection of the overloaded components, the reduction in efficiency was said to be overcome somewhat.

Costa Neto, C., et al., Programmed Flow Gas Chromatography, Journal of Chromatography, Vol. 15 (1964) pp. 301-313 discusses the utilization of a programmed flow of GC mobile phase in isothermic or temperature programmed runs, in order to obtain the separation of complex mixtures. Theoretical derivations of equations relating flow rate to various chromatogram properties such as peak migration, peak width, peak area and peak height are discussed. Flow rate in relation to efficiency and resolution is also discussed. The programmed flow actually used by the authors was said to be manual in nature using a step valve.

Zlatkis, A., Flow Programming—A New Technique in Gas Chromatography, Journal of Gas Chromatography (Mar. 1965), pp. 75-81 discusses the use of a pneumatically regulated flow controller for regulating flow rate in an exponential fashion between preset limits. In reviewing previous flow programming reports, such as the Costa Neto reference discussed above, Zlatkis et al. characterizes that reference as only discussing flow programming in relation to so called preparative gas chromatography as opposed to practical analytical gas chromatography.

Nygren, S. et al., Flow Programming in Glass Capillary Column-Electron Capture Gas Chromatography by Using the Valve in the Splitter Line, Journal of Chromatography, Vol. 123 (1976) pp. 101–108 discusses flow programming through the use of a metering valve in the side outlet of an inlet splitter. It was said that by exponentially programming carrier gas flow, under certain circumstances, results could be achieved which were comparable to temperature programming.

More recently, Larson, J. R. et al., Flow Programming System for Process Capillary Gas Chromatography, Journal of Chromatography, Vol. 405 (1987) pp. 163–168 discusses a continuous flow programming technique for process capillary gas chromatography which processes do not have temperature programming capabilities. It was concluded that by programming carrier gas flow in a process GC application, shorter cycle times could be achieved than temperature programmed GC devices.

The problem with each of the above flow programming devices lies in that carrier gas flow and/or temperature programming are independently operated, i.e. closed loop systems. As such, these systems are operated exclusive of each other. Such devices cannot assure constant column efficiency or constant mass flow. The major drawbacks of such closed loop flow control systems are limited dynamic range, the need for flow sensing and changes or drifts in the calibration of the flow sensor. Changes or drift in calibration can be caused by the contamination of the flow sensor.

Additionally, such independently operated closed loop systems are incapable of detecting undesirable conditions affecting the accuracy of the chromatographic analysis and of making adjustments to avoid such conditions. For example, for a given temperature program, a desired flow characteristic may not be possible within the GC system parameters. The above described devices are not capable of determining or sensing the failure of the device to achieve the desired flow characteristic.

It has been discovered that through the use of the open loop flow control system of the present invention, not only can the problems of prior temperature and flow programming devices be overcome, but also, the molecular weight range of compounds capable of GC analysis can be extended. As used in this application the phrase open loop flow control system signifies that there is no direct feedback of the controlled parameter. In open loop flow control there is no flow sensing operation, only pressure sensing and computation of desired pressure to give calculated flow.

SUMMARY OF THE INVENTION

The advantages of the invention are achieved in a method and apparatus for performing a chromatographic separation of a given compound utilizing programmed temperature and mass flow wherein the compound is injected into a pressurized carrier gas and passed through a column and wherein a portion of the column is subjected to a temperature profile, by determining the pressure of the carrier gas and generating a pressure information signal representative of such pressure, storing desired carrier gas mass flow information and temperature profile information, and controlling the pressure of the carrier gas in response to the mass flow information, the temperature profile information and the pressure information signal, so that as the temperature profile information changes with time, the desired mass flow of carrier gas at a corresponding time is maintained by controlling the pressure of the carrier gas.

BRIEF DESCRIPTION OF THE DRAWINGS

The present invention will be better understood, and its numerous objects and advantages will become apparent by reference to the following detailed description of the invention when taken in conjunction with the following drawings, in which:

FIG. 5 is a flow chart showing the operations performed by the controller shown in FIG. 3.

DETAILED DESCRIPTION

Figure 1:
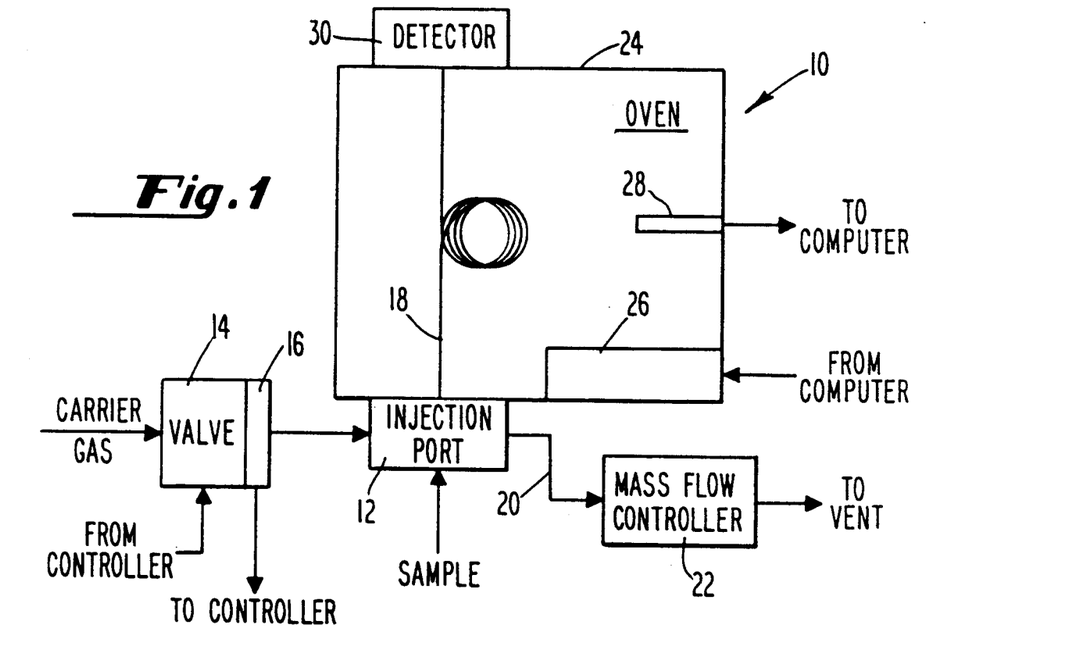
FIG. 1 is a block diagram of a forward pressure regulated gas chromatograph constructed in accordance with the present invention.

A new and novel gas chromatograph is shown in FIG. 1 and is generally designated 10. As shown in FIG. 1, chromatograph 10 is arranged in a forward pressure regulated design suitable for direct, i.e. non-split, injections. In order to perform a chromatographic separation of a given sample compound, the sample is injected into a pressurized carrier gas by means of an injection port 12. The carrier gas supplied to injection port 12 is first provided from a source (not shown) to valve 14. Valve 14 serves to control the pressure of the carrier gas processor in the GC system. A pressure transducer 16 generates a pressure information signal representative of the carrier gas provided to injection port 12. The pressure information signal is an electronic signal which is provided to a controller which will be described in greater detail in relation to FIG. 3. Valve 14 regulates carrier gas pressure in response to a control signal, the generation of which will be described in greater detail in relation to FIG. 5. Although the particular design of valve 14 is not critical to the present invention, in the preferred embodiment a Model Number 001-1014 pressure valve sold by Porter Instrument Company, Inc. of Hatfield, Pa. is preferred.

Injection port 12 provides a portion of the carrier gas/sample combination to column 18 with the remainder passing through a non-analyzed output 20. The flow exiting output 20 is known as the septum purge flow. By maintaining a relatively constant low purge flow (5–15 ml/min.) through mass flow controller 22, it is possible to minimize "false" peaks from the injection port septum (not shown) and also minimize air diffusion into the column.

By incorporating mass flow controller 22, a greater flow of carrier gas can be utilized which in turn allows valve 14 to be operated in a region which is easier to control. For example, instead of using the valve to control the flow of carrier gas in the region of approximately one milliliter per minute, the valve can instead be operated in a range of approximately ten milliliters per minute while still providing the same amount of carrier gas/sample combination to column 18.

As shown in FIG. 1, column 18 is positioned within oven 24. Although no particular oven design is necessary in order to comply with the principles of the present invention, the oven should include a heating unit 26 and a temperature sensor 28. Heating unit 26 provides heat to oven 24 in response to a control signal generated by a computer which will be described in greater detail in relation to FIG. 3. In order to ensure that the temperature within the oven is at a desired level, sensor 28 generates a feedback signal representative of the temperature in oven 24, which signal is provided to the computer shown in FIG. 3. The carrier gas/sample combination passing through column 18 is exposed to a temperature profile resulting from the operation of heater 26 within oven 24. Typically, the temperature in oven 24 is increased from a minimum level to a maximum level in a linear and non-linear fashion. During this profile of changing temperatures, i.e., rising or falling, the sample will separate into its components primarily due to differences in the volatility characteristics of each component at a given temperature. As the components exit column 18 they are detected by detector 30. Detector 30 can be any of the known GC detectors such as a flame ionization detector or a mass spectrometer.

Chromatograph 10, as shown in FIG. 1, is said to be a forward pressure regulated gas chromatograph because valve 14 is regulating the pressure of the carrier gas forward from (downstream of) the control valve. Without departing from the principles of the present invention, pressure of the carrier gas can also be regulated according to a back pressure regulated mode, wherein the pressure is regulated back from (upstream of) the control valve, shown in FIG. 2.

Figure 2:
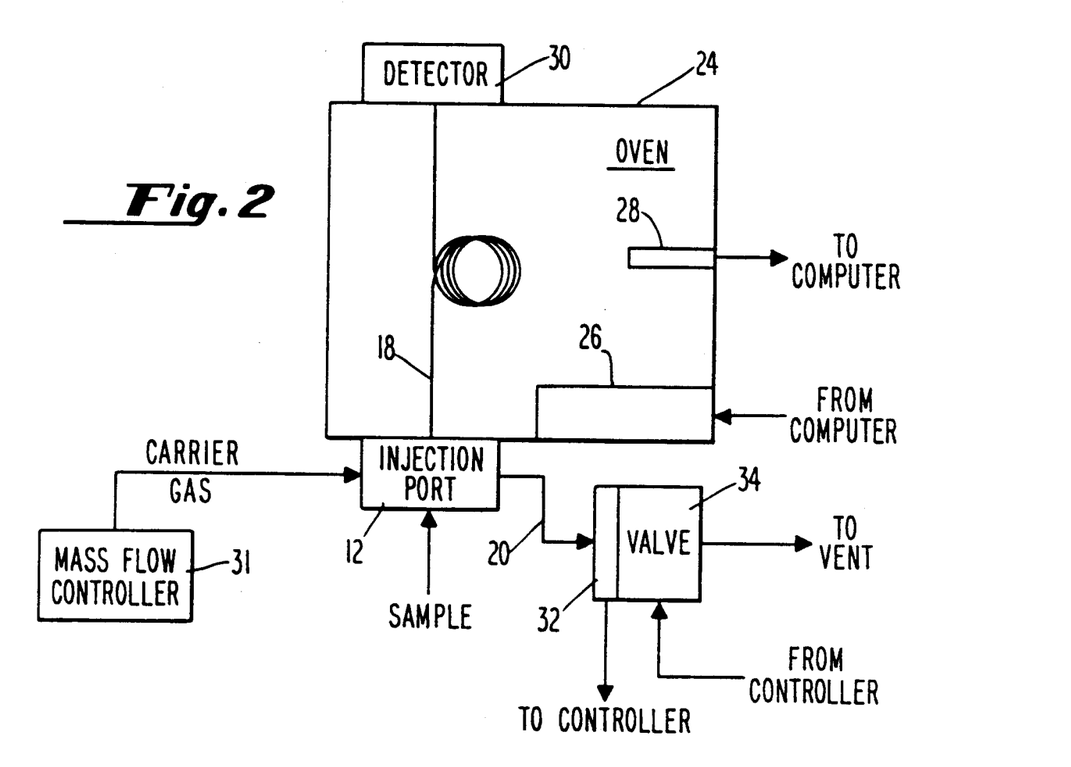
FIG. 2 is a block diagram of a back pressure regulated gas chromatograph constructed in accordance with the present invention.

As shown in FIG. 2, the chromatograph is arranged in a back pressure regulated design suitable for so-called splitter or split injections. In a split injection, a portion of the sample to be analyzed is injected onto the column while the remainder of the sample is "split" off the column and directed out the vent. Such split injection techniques would include so-called hot split, hot splitless, cold split and cold splitless injection techniques.

As depicted in FIG. 2, the total carrier gas is provided directly to injection port 12 from mass flow controller 31. The pressure of the carrier gas is determined by pressure transducer 32 which senses the pressure of the carrier gas/sample combination in the non-analyzed output 20. The pressure of the carrier gas is controlled by valve 34 in response to an appropriate signal from the controller described in relation to FIG. 3. The ratio between that portion of the sample/carrier gas provided to output 20 and the remainder provided to column 18 is known as the split ratio. The split ratio regulates the amount of the carrier gas/sample combination which passes through column 18. By operation of valve 34 the pressure of the carrier gas in column 18 is controlled. As will be seen hereinafter, controlling the pressure in column 18 results in controlling the flow in column 18.

The electronic controls utilized in accordance with the principles of the present invention to operate the chromatographs shown in FIGS. 1 and 2 will hereafter be described. It will first be noted, however, that the present invention is an advance over other GC systems because, for the first time, implementation of desired mass flow characteristics exhibited during an analysis have been directly related to temperature, i.e. oven temperature. This relationship is achieved by regulating the carrier gas pressure as a function of carrier gas absolute viscosity for a given oven temperature, system parameters, and desired mass flow. Such regulation is achieved primarily in the electronic controls to be described herein where a pressure set point and control voltage are established and used to control valves 14 and 34.

Figure 3:
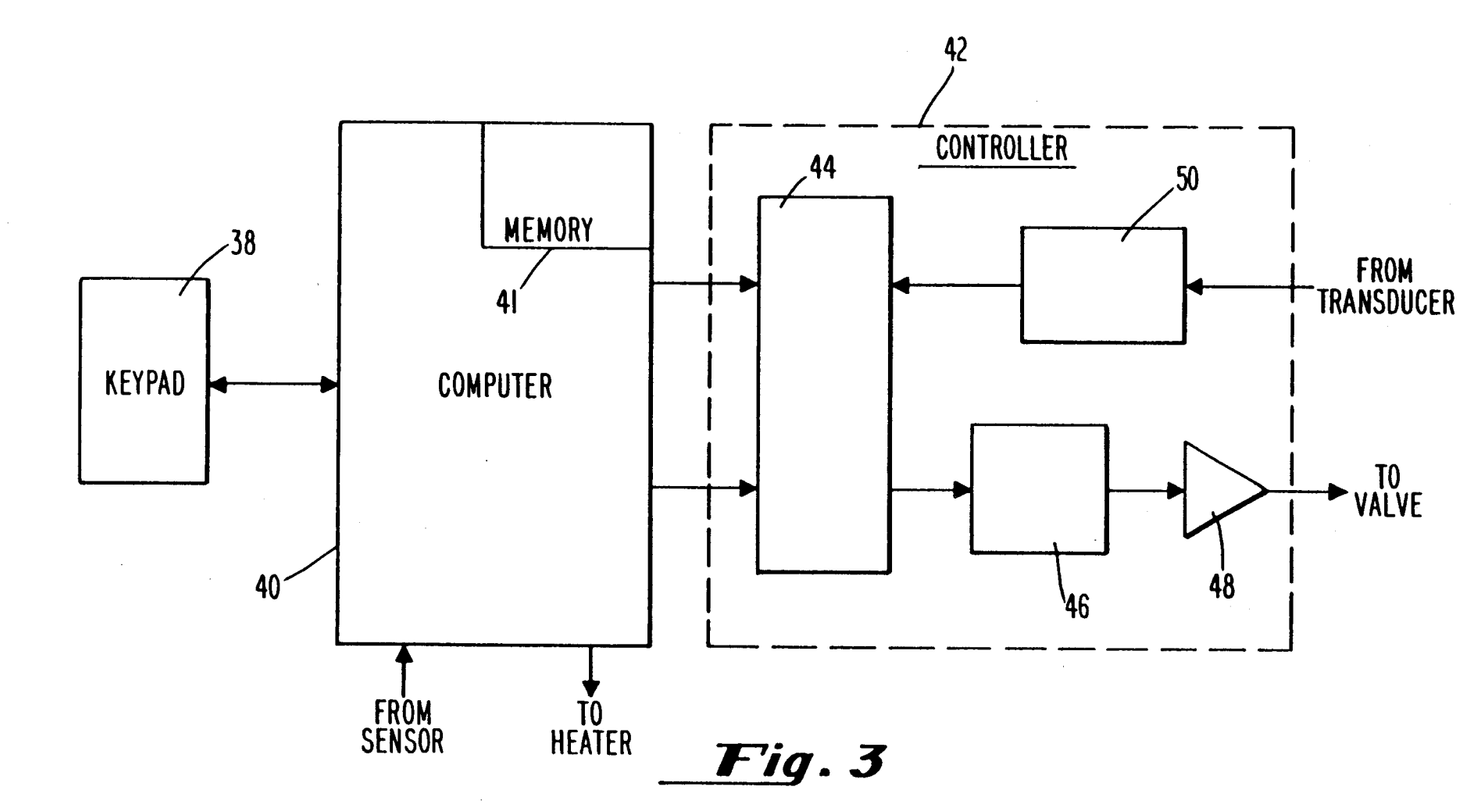
FIG. 3 is a block diagram of the electronic circuit utilized to operate and control the gas chromatographs shown in FIGS. 1 and 2.

Referring to FIG. 3, the electronic controls are shown to include three main components, namely keypad 38, computer 40 and controller 42. Computer 40 maintains overall control of all systems associated with gas chromatograph 10. It will be recognized that any particular gas chromatograph may include more systems than those described in relation to the present invention. It will also be understood that although computer 40 is shown as a single block, such computer includes a central processing unit and all associated peripheral devices, such as random access memories, read-only memories, input/output isolation devices, clocks and other related electronic components. In the preferred embodiment, the central processor used in computer 40 is a Z80 microprocessor. As such, computer 40 includes a memory 41 in which information and programming can be stored and retrieved by known methods. The programming associated with computer 40 which is utilized in relation to the present invention will be described in greater detail in connection with FIG. 4.

One of the functions of computer 40 is the control of oven temperature. Computer 40 controls oven temperature by transmitting an appropriate signal to heater 26 which causes heater 26 to increase or decrease the amount of heat transferred to oven 24. Sensor 28 senses the temperature in oven 24 and transmits a feedback signal representative of such temperature to computer 40. By monitoring the temperature feedback signal from sensor 28 computer 40 can maintain the temperature in oven 24 at some desired level by controlling heater 26. Operating commands and other information are entered into computer 40 by way of keypad 38. The particular information entered through keypad 38 which relates to the present invention will be described in relation to FIG. 4. Keypad 38 in the preferred embodiment is provided with a display screen. Consequently, indicating or prompt messages can be generated by computer 40 and displayed on keypad 38.

A controller circuit 42 is utilized to control either valve 14 or 34. Controller 42 is shown to include a second computer 44, which in the preferred embodiment incorporates a 6809 Motorola microprocessor and its associated peripheral components. The programming utilized to operate computer 44 in accordance with the present invention is described in greater detail in relation to FIG. 5.

Computer 44 in the preferred embodiment generates a control signal which is used to control valves 14 and 34. Since the generated control signal is in a digital form it is converted to analog form by digital to analog converter 46 and appropriately amplified by amplifier 48 prior to transmission to valve 14 or 34. As will be described in greater detail in relation to FIG. 5, the carrier gas pressure as sensed by transducer 16 or 32 is provided to computer 44 by first converting the analog signal generated by the pressure transducer from analog to a digital signal by converter 50. The digital signal generated by converter 50 is supplied to computer 44.

Figure 4:
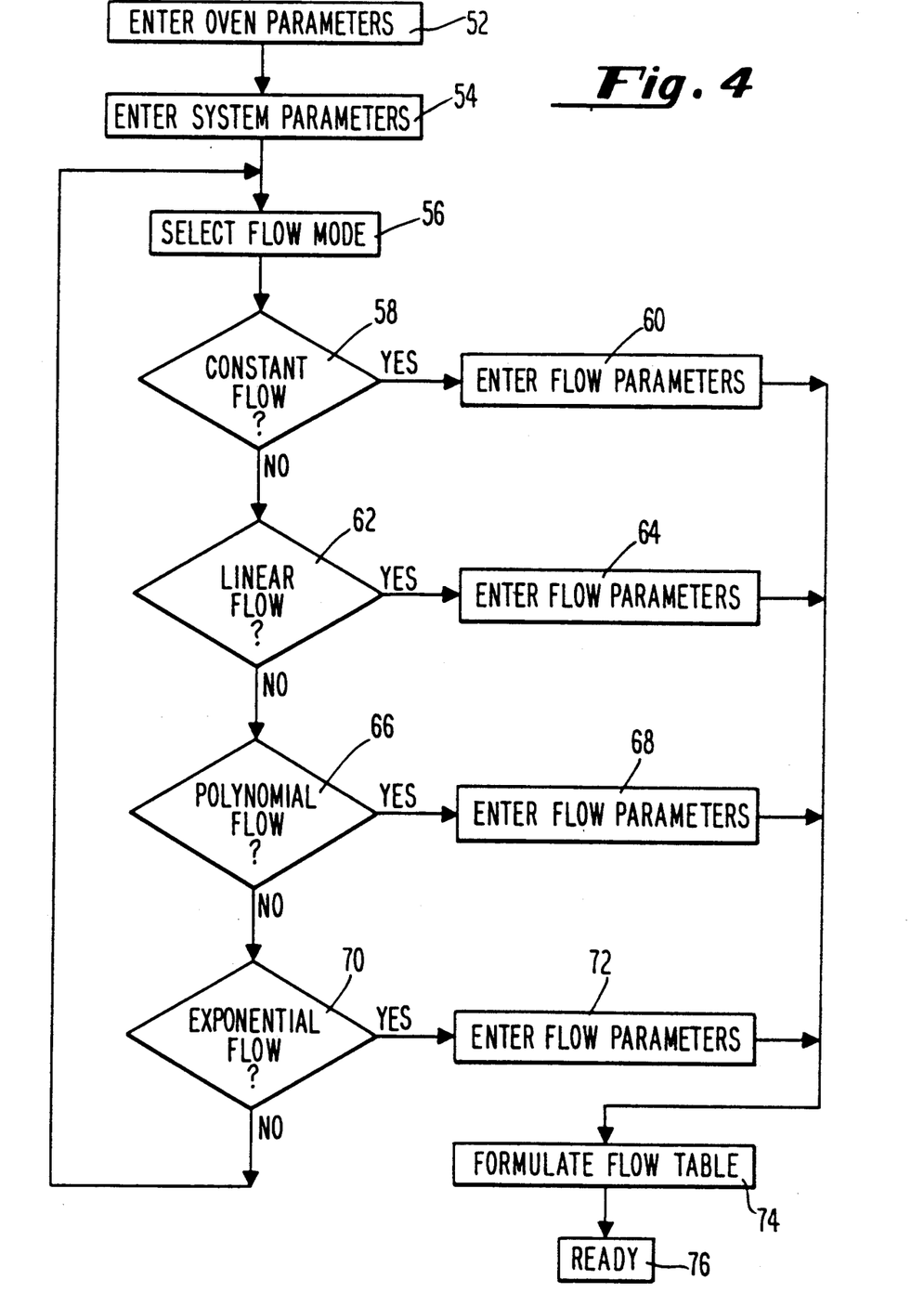
FIG. 4 is a flow chart of a portion of the operations performed by the computer shown in FIG. 3.

Consider now that portion of the operation of computer 40 which relates to and is in accordance with the present invention. Referring to FIG. 4, there will be described those procedures necessary to program or set the GC system so that a particular gas chromatographic separation test or run can be conducted. Several pieces of information are entered into computer 40 by the user through way of keypad 38. With one processing exception which will be described, computer 40 operates to store the entered information into memory 41 for later access by computer 44. As will become apparent, certain of the information stored in memory 41 will be stored in a time sequential format.

Initially parameters relating to the temperature profile to be provided by oven 24 during the analysis are entered at step 52. In the preferred embodiment, desired oven temperature for any given moment in time during the analysis is calculated by computer 40 in relation to the oven temperature parameters. In the preferred embodiment, such oven temperature calculation is performed at a rate of 40 Hz. Basically, each item of temperature information represents the desired temperature of oven 24 at a particular point in time during a chromatographic analysis. Accordingly, it will be necessary to enter an initial oven temperature and an initial oven time, a final oven temperature and a final oven time and the rate at which it is desired for the oven temperature to proceed from the initial temperature to the final temperature for the time period existing between the initial time and the final time. Having entered this information, it is a relatively simple operation for computer 40 to generate a desired oven temperature in real time. To regulate the temperature of oven 24, the calculated desired oven temperature is used as a control signal.

System parameters are entered via keypad 38 into computer 40 at step 54. In the preferred embodiment the system parameters which are necessary for entry include the type of carrier gas utilized, such as helium, nitrogen or hydrogen, etc. System parameters would also include the length and diameter of column 18, and column outlet pressure if different than one (1) atmosphere, i.e. a vacuum. In the preferred embodiment it is also desirable to enter a calibration factor. The calibration factor is related to the actual length and nominal column inner diameter. Such lengths and diameters may in fact differ by several percent between columns with identical length and diameter specifications. A given column can be calibrated by timing the period a so-called unretained peak, such as the detection of $CH_4$, takes to pass through a column at a given pressure setting.

In developing the calibration factor, one could also look at pressure transducers 16 and 32. In the preferred embodiment, transducers 16 and 32 are 1210-A100G3L transducers sold by I.C. Sensors of Milpitas, Calif. Generally, these pressure transducers will not need calibration as their linear specifications are as good or better than most pressure calibration systems. It will be recognized, however, that the so-called zero offset will need to be corrected. Such an auto-zeroing operation of the pressure transducer at each power turn-on can be performed by any known method.

At step 56 the user selects the desired mass flow mode. The mass flow mode is the type of mass flow which is to be exhibited by the carrier gas as it passes through column 18. As shown in FIG. 4 the flow mode of the carrier gas can be either a constant mass flow, a linear mass flow, a polynomial mass flow, or an exponential mass flow. The mass flow mode can also be referred to as the mass flow profile.

At step 58 it is determined whether constant flow has been selected. If constant mass flow has been selected, the constant flow parameters are entered at step 60. In the preferred embodiment, the constant flow parameters include the initial set point pressure, i.e., the initial point at which the carrier gas pressure will be set, initial oven temperature and the outlet pressure ($P_o$). The outlet pressure represents the pressure at the end of column 18 where the carrier gas/sample combination is deposited into detector 30. Depending on the type of detector used, the outlet pressure will either be one atmosphere or at a pressure near absolute zero, for example, if a mass spectrometer-type detector is utilized. If the constant mass flow mode has not been selected at step 56, computer 40 proceeds to step 62 to determine whether linear mass flow has been selected.

If linear mass flow has been selected, it is necessary to enter the linear mass flow parameters at step 64. Linear mass flow parameters will include entry of the initial mass flow rate, the initial time, a ramp rate, a final mass flow rate and a final time. The ramp rate is that rate at which mass flow of carrier gas will increase between the initial time and the final time. If linear mass flow has not been selected, the computer will next determine at step 66 whether a polynomial mass flow mode has been selected.

If a polynomial mass flow mode has been selected, it will be necessary to enter the polynomial mass flow mode parameters at step 68. Polynomial mass flow mode parameters will include the initial flow rate, the initial time, the ramp coefficient, the ramp exponent, the final flow rate and the final time. If the polynomial mass flow mode has not been selected, the computer will determine at 70 whether the exponential mass flow mode has been selected.

If the exponential mass flow mode has been selected, it will be necessary to enter the exponential mass flow mode parameters at 72. The exponential mass flow mode parameters include the initial flow rate, the initial time, the exponential time constant, the final flow rate and the final time. If exponential mass flow mode has not been selected, the computer will return to step 56 in order for the user to enter a mass flow mode.

In the preferred embodiment it is desirable to have computer 40 prompt the user by displaying various questions on keypad 38 related to the selection of carrier gas mass flow mode and the various mass flow parameters. Having entered the various flow parameters, computer 40 will formulate a flow table at step 74. The formulation of a flow table is a relatively simple operation since it is a collection of desired flow values arranged in a time sequential format. For example, consider the formulation of a flow table in relation to linear flow parameters. Since computer 40 knows the initial flow, the final flow and the ramp rate, it can easily calculate desired flow values over the course of the time period between the initial time and the final time. Such information is arranged in a time sequential format. It should be noted that if constant mass flow has been selected it is merely necessary to provide the information entered in relation to constant flow to computer 44, namely the initial pressure, initial oven temperature and the outlet pressure.

Although not shown, it is necessary that viscosity information associated with the particular carrier gas to be utilized has previously been entered into memory 41 of computer 40. Such information would include the absolute viscosity of the particular carrier gas for various temperatures. The temperature range over which such viscosities need be given directly corresponds to the temperature range or temperature profile to be exhibited by oven 24.

Having formulated the flow information table, computer 40 now gives an indication that it is ready to begin a gas chromatography analysis run at step 76.

Once the GC analysis has begun, the operation of the present invention is primarily controlled by controller 42. Referring to FIG. 5, the GC analysis is started at block 78. This start can either be achieved by an indication from computer 40 that all system and flow information has been assembled or can be achieved by the user entering an appropriate command on keypad 38. It will be recognized that the programming depicted in FIG. 5 is, in fact, stored in the peripheral memory devices associated with computer 44, which in the preferred embodiment would be the memory devices typically associated with a 6809 Motorola microprocessor.

At step 80, computer 44 gets the runtime and actual oven temperature from computer 40. It will be recalled that computer 40 is sampling the signal generated by temperature sensor 28, which signal is representative of the actual oven temperature. Having the time and temperature information, computer 44 next gets the flow information associated with that time from the tables stored in memory 41 at step 82. Although the oven temperature information can come from several sources, for example the sensed oven temperature signal generated by sensor 28 is preferred, the oven temperature information used to generate the control signal for heater 26 could also be utilized. At step 84, computer 44 reads the pressure determined by the pressure transducer 16 or 32. It will be recalled that the signal generated by transducer 16 or 32 is passed through analog to digital converter 50. Having gotten the oven and flow information for the particular time value and having read the pressure sensed by transducer 16 or 32, computer 44 determines whether the constant mass flow mode has been selected by the user at step 86.

If the constant mass flow mode has been selected, computer 44 gets the carrier gas viscosity information from computer 40 at 88. It will be recalled that viscosity information for the carrier gas had been previously entered into the memory of computer 40 such that for any given oven temperature a viscosity value was associated therewith. At step 88, computer 44 has already obtained oven temperature information and retrieves the viscosity information from computer 40 associated with that oven temperature. Computer 44 at step 90 obtains the outlet pressure from computer 40 which was originally entered by the user through keypad 38. Computer 44 is now in a state where it can calculate the pressure set point ($P_{setpt}$).

Since the flow mode selected is a constant flow, $P_{setpt}$ is calculated according to the following formulae:

$$In = \frac{\pi d^4}{256 \cdot L} \cdot \rho s \cdot \frac{Ts}{Tc} \cdot \frac{[Pi^2 - Po^2]}{Ps} \cdot \frac{1}{\mu(Tc)} = C \quad (1)$$

where:
$\mu(Tc)$ = absolute viscosity of carrier gas at column temperature
$Tc$ = Column Temperature (Absolute Temperature)
$Ts$ = Standard Ambient Temperature (Absolute Temperature)
$\rho s$ = Density of carrier gas at standard pressure and temperature
$d$ = Column diameter
$L$ = Column length
$Pi$ = Inlet Pressure—converted to Absolute Pressure
$Po$ = Outlet Pressure—converted to Absolute Pressure
$Ps$ = Standard Ambient Pressure ($Ps = 1$ atm = 760 torr)
$In$ = Mass Flow Rate = C (Constant)

$$K = \frac{\pi d^4 \rho s \, Ts}{256 \, L \, Ps} \quad (2)$$

$$In = K \cdot \frac{[Pi^2 - Po^2]}{Tc \cdot \mu(Tc)} = C \quad (3)$$

$$P_{setpt} = Pi = \left[\frac{C}{K} \cdot Tc \cdot \mu(Tc) + Po^2\right]^{\frac{1}{2}} \quad (4)$$

As Tc (Column Oven Temperature) changes, Pi (Inlet Pressure) is changed per this equation.

Flow never needs to be calculated in Constant Flow Mode; it only needs to be kept constant. Knowing the desired mass flow, the pressure set point calculation at step 92 can be completed using equation 1.

If at step 86 it is determined that constant mass flow has not been selected, computer 40 retrieves viscosity and system parameter information at step 94. Having retrieved flow information at 82 and having retrieved the viscosity and system parameter information, the $P_{setpt}$ can now be calculated at step 96.

The calculation of the $P_{setpt}$ for flow modes other than constant mass flow is achieved using the following formulae: Rederiving equation (4) from page 22, and with $In_{setpt}$ = Mass Flow Setpoint, $$K = \frac{\pi d^4 \rho s \, Ts}{256 \, L \, Ps} \quad (5)$$

$$In_{setpt} = \frac{K \cdot [Pi^2 - Po^2]}{Tc \cdot \mu(Tc)} \quad (6)$$

$$P_{setpt} = Pi = \left[\frac{In_{setpt}}{K} \cdot Tc \cdot \mu(Tc) + Po^2\right]^{\frac{1}{2}} \quad (7)$$

It will be recognized that depending upon the units used in the entry of information through keypad 38 that a correction constant may be necessary in order to ensure that the $P_{setpt}$ calculation is correctly performed. In other words, if whole numbers are used to enter a column diameter such as the number 320 representing microns, it will be necessary to enter a correction constant factor of $10^{-6}$.

$In_{setpt}$ will be equal to the mass flow value obtained by computer 44 from memory 41 of computer 40 at step 82 and the absolute viscosity will be equal to the viscosity information obtained by computer 44 in relation to the oven temperature information retrieved at step 80. Having calculated the $P_{setpt}$ at step 96 using equation 3, computer 44 next generates a control voltage signal at step 98.

In the preferred embodiment, computer 44 utilizes a PID control algorithm scheme for calculating the control voltage at step 98. Such control techniques are not new, however, their application to the control of carrier gas pressure in gas chromatography equipment is believed to be novel. PID control is a proportional-integral-derivative control scheme whereby an actuating signal represents a weighted sum of the difference, time integral of the difference and time derivative of the difference, between an input and output. In relation to the present invention, the control voltage is calculated by first determining the proportional term. If a forward pressure regulated configuration, shown in FIG. 1, is utilized, the proportional term is calculated by subtracting the pressure value determined by transducer 16 from the $P_{setpt}$ value calculated at step 96. If back pressure regulation, shown in FIG. 2, is utilized, then the proportional term is calculated by substracting the $P_{setpt}$ determined at step 96 from the pressure measured by transducer 32.

Next, the integral of the proportional term is determined. The integral is merely the sum of all proportional terms during the particular GC analysis. The derivative term is calculated by subtracting the prior proportional term from the present proportional term. After the proportional term, the integral and derivative have been determined, the control voltage is calculated according to the following formula:

$$\text{Control voltage} = P^*a + I^*b + D^*c \qquad (8)$$

It will be noted that each of the terms in the control voltage equation are modified by the values A, B and C. A, B and C are terms used to optimize the PID control scheme and are determined using known methods. In practice, the terms A, B and C are used to so-called tweak the system in order to achieve optimum results. Having determined the control voltage using equation 4, computer 44 next determines whether the gas chromatograph has been set with conditions which are not achievable.

At step 100 computer 44 determines whether the calculated control voltage exceeds a reference voltage. If the calculated voltage exceeds a reference it can be deduced that the user has entered flow conditions which cannot be achieved. Computer 44 sends a signal at step 102 to computer 40 indicating that the desired mass flow cannot be reached because the pressure necessary to achieve such mass flow is too great or exceeds the present system configuration. Having sent such a signal to computer 40, computer 44 brings its operation to an end at step 104.

If the calculated control voltage does not exceed the reference voltage, computer 44 next determines at step 106 whether the run time is equal to 0. If the answer is yes, the GC analysis is at an end and computer 44 ends its operation at step 108. If run time does not equal to 0, computer 44 outputs the calculated control voltage signal and loops back to step 80 to get the next sequential time information from computer 40. As previously indicated, the transmission of the control voltage is achieved by first passing the digital signal through digital to analog converter 46 and thereafter appropriately amplifying the analog signal in the amplifier 48. The amplified analog signal is then presented to either valve 14 or valve 34.

While the invention has been described and illustrated with reference to specific embodiments, those skilled in the art will recognize that modification and variations may be made without departing from the principles of the invention as described herein above and set forth in the following claims.

What is claimed is:

1. A method for performing a chromatographic separation of a given compound wherein said compound is injected into a pressurized carrier gas and passed through a column and wherein a portion of said column subjected to a temperature profile, comprising the steps of:
    generating a temperature information signal representative of the temperature to which said column is subjected;
    determining the pressure of said carrier gas and generating a pressure information signal representative of said pressure;
    storing system information, mass flow information, and carrier gas viscosity information;
    retrieving said system information, said mass flow information and said viscosity information and calculating a carrier gas pressure in relation to said system information, said mass flow information and said viscosity information;
    generating a control signal in relation to the calculated carrier gas pressure and said pressure information signal; and
    controlling the pressure of said carrier gas in response to said control signal, so that as the temperature to which said column is subjected changes with time, the desired mass flow of carrier gas at a corresponding time is maintained by controlling the pressure of said carrier gas.

2. The method of claim 1, wherein said sample is injected into said carrier gas through an injection port, and wherein the pressure of said carrier gas is controlled upstream from said injection port.

3. The method of claim 1, wherein said sample is injected into said carrier gas through an injection port, and wherein the pressure of said carrier gas is controlled downstream from said injection port.

4. The method of claim 1, wherein the step of generating a temperature information signal further comprises the steps of entering data representative of desired oven temperature in relation to time into a first computer, and controlling the temperature to which said column is subjected by said first computer in response to said data, wherein said temperature information signal is representative of said data.

5. The method of claim 4, wherein said system information, mass flow information, and carrier information is also stored in said first computer.

6. The method of claim 5, wherein the pressure of said carrier gas is controlled by a valve and wherein the step of determining the pressure of said carrier gas comprises the step of providing a pressure transducer positioned proximate said valve.

7. The method of claim 1, wherein said step of calculating a carrier gas pressure is accomplished according to the formula:

$$P_{setpt} = Pi = \left[ \frac{In_{setpt}}{K} \cdot Tc \cdot \mu(Tc) + Po^2 \right]^{\frac{1}{2}}$$

$$K = \frac{\pi d^4\, ps\, Ts}{256\, L\, Ps}$$

Tc = Column Temperature (Absolute Temperature)
Ts = Standard Ambient Temperature (Absolute Temperature)

ρs = Density of carrier gas at standard pressure and temperature
d = Column diameter
L - Column length
Pi = Inlet Pressure - converted to Absolute Pressure
Po = Outlet Pressure - converted to Absolute Pressure
Ps = Standard Ambient Pressure (Ps = 1 atm = 760 torr)
In$_{setpt}$ = The Mass Flow Set Point
μ(Tc) = Absolute Viscosity.

8. The method of claim 7, wherein the step of generating a control signal comprises the steps of providing a PID control algorithm, and generating said control signal using said PID algorithm in relation to P$_{setpt}$ and said pressure information signal.

9. The method of claim 1, further comprising the steps of comparing said control signal to a reference value and indicating when said control signal exceeds said reference value.

10. A method for performing a chromatographic separation of a given compound wherein said compound is injected into a pressurized carrier gas and passed through a column and wherein a portion of said column is subjected to a temperature profile, comprising the steps of:
determining the pressure of said carrier gas and generating a pressure information signal representative of said pressure;
storing desired carrier gas mass flow information and temperature profile information; and
controlling the pressure of said carrier gas in response to said flow information, said temperature profile information and said pressure information signal, so that as said temperature profile information changes with time, the desired mass flow of carrier gas at a corresponding time is maintained by controlling the pressure of said carrier gas.

11. An apparatus for performing a chromatographic separation of a given compound wherein said compound is injected into a pressurized carrier gas and passed through a column and wherein a portion of said column is contained in an oven which subjects the column to a temperature profile, comprising:
temperature means for generating a temperature information signal representative of the temperature in said oven;
pressure means for determining the pressure of said carrier gas and for generating a pressure information signal representative of said pressure;
memory means for storing system information, mass flow information, and carrier gas viscosity information;
control means for receiving said temperature information signal and said pressure information signal, for retrieving said system information, said mass flow information and said viscosity information from said memory means, for calculating a carrier gas pressure in relation to said system information, said mass flow information and said viscosity information, and for generating a control signal in relation to the calculated carrier gas pressure and said pressure information signal; and
valve means for controlling the pressure of said carrier gas in response to said control signal, so that as the temperature in said oven changes with time, the desired mass flow of carrier gas at a corresponding time is maintained by controlling the pressure of said carrier gas.

12. The apparatus of claim 11, further comprising an injection port, wherein said sample is injected into said carrier gas by said injection port, and wherein said valve means is positioned upstream from said injection port.

13. The apparatus of claim 11, further comprising an injection port, wherein said sample is injected into said carrier gas by said injection port, and wherein said valve means is positioned downstream from said injection port.

14. The apparatus of claim 11, wherein said temperature means comprises a temperature sensor positioned to sense the temperature in said oven and for generating said temperature information signal representative of the temperature in said oven.

15. The apparatus of claim 14, wherein said memory means comprises a part of said control means.

16. The apparatus of claim 11, wherein said pressure means comprises a pressure transducer positioned proximate said valve means.

17. The apparatus of claim 11, wherein said control means comprises a computer and wherein said carrier gas pressure is calculated according to the formula:

$$P_{setpt} = Pi = \left[ \frac{In_{setpt}}{K} \cdot Tc \cdot \mu(Tc) + Po^2 \right]^{\frac{1}{2}}$$

$$K = \frac{\pi d^4 \rho s \, Ts}{256 \, L \, Ps}$$

where
Tc = Column Temperature (Absolute Temperature)
Ts = Standard Ambient Temperature (Absolute Temperature)
ρs = Density of carrier gas at standard pressure and temperature
d = Column diameter
L - Column length
Pi = Inlet Pressure - converted to Absolute Pressure
Po = Outlet Pressure - converted to Absolute Pressure
Ps = Standard Ambient Pressure (Ps = 1 atm = 760 torr)
In$_{setpt}$ = The Mass Flow Set Point
μ(Tc) = Absolute Viscosity.

18. The apparatus of claim 17, wherein said control signal is generated by a PID control algorithm, and wherein said control signal is generated in relation to P$_{setpt}$ and said pressure information signal.

19. The apparatus of claim 11, further comprising comparison means for comparing said control signal to a reference value and indication means for indicating when said control signal exceeds said reference value.

20. An apparatus for performing a chromatographic separation of a given compound wherein said compound is injected into a pressurized carrier gas and passed through a column and wherein a portion of said column is contained in an oven which subjects the column to a temperature profile, comprising:
pressure means for determining the pressure of said carrier gas and for generating a pressure information signal representative of said pressure;
memory means for storing desired carrier gas mass flow information and oven temperature information; and control means for retrieving said mass flow information and said oven temperature information and for controlling the pressure of said carrier gas in response to said mass flow information, said oven temperature information and said pressure information signal, so that as said oven temperature information changes with time, the desired mass flow of carrier gas at a corresponding time is maintained by controlling the pressure of said carrier gas.

21. An apparatus for performing a chromatographic separation of a given compound wherein said compound is injected into a pressurized carrier gas and passed through a device having a controlled temperature which subjects the carrier gas to a temperature profile, comprising:
   temperature means for generating a temperature information signal representative of the temperature in said device;
   pressure means for determining the pressure of said carrier gas and for generating a pressure information signal representative of said pressure;
   memory means for storing system information, mass flow information, and carrier gas viscosity information;
   control means for receiving said temperature information signal and said pressure information signal, for retrieving said system information, said mass flow information and said viscosity information from said memory means, for calculating a carrier gas pressure in relation to said system information, said mass flow information and said viscosity information, and for generating a control signal in relation to the calculated carrier gas pressure and said pressure information signal.

22. The apparatus of claim 21, wherein said control means generates said control signal so that the mass flow of said carrier gas is modified linearly during a portion of said chromatographic separation.

23. The apparatus of claim 21, wherein said control means generates said control signal so that the mass flow of said carrier gas is modified in a polynomial fashion during a portion of said chromatographic separation.

24. The apparatus of claim 21, wherein said control means generates said control signal so that the mass flow of said carrier gas is modified exponentially during a portion of said chromatographic separation.

25. The apparatus of claim 21, wherein said control means generates said control signal so that the mass flow of said carrier gas is maintained relatively constant during a portion of said chromatographic separation.

* * * * *